US006479064B1

(12) United States Patent
Atala

(10) Patent No.: US 6,479,064 B1
(45) Date of Patent: Nov. 12, 2002

(54) CULTURING DIFFERENT CELL POPULATIONS ON A DECELLULARIZED NATURAL BIOSTRUCTURE FOR ORGAN RECONSTRUCTION

(75) Inventor: Anthony Atala, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/474,525

(22) Filed: Dec. 29, 1999

(51) Int. Cl.[7] .......................... A61F 2/00; C12N 11/02; C12N 11/08; C12N 5/06; C12N 5/08

(52) U.S. Cl. ...................... 424/423; 424/93.7; 435/177; 435/180; 435/395

(58) Field of Search ............................... 424/93.7, 423; 435/177, 180, 395

(56) References Cited

U.S. PATENT DOCUMENTS

| | | | |
|---|---|---|---|
| 4,458,678 A | 7/1984 | Yannas et al. | 128/155 |
| 4,520,821 A | 6/1985 | Schmidt et al. | 128/334 |
| 4,963,489 A | 10/1990 | Naughton et al. | 435/240.1 |
| 5,032,508 A | 7/1991 | Naughton et al. | 435/32 |
| 5,160,490 A | 11/1992 | Naughton et al. | 435/284 |
| 5,429,938 A | 7/1995 | Humes | 435/240.2 |
| 5,443,950 A | 8/1995 | Naughton et al. | 435/1 |
| 5,516,680 A | 5/1996 | Naughton et al. | 435/240.243 |
| 5,549,674 A | 8/1996 | Humes et al. | 623/11 |
| 5,567,612 A | 10/1996 | Vacanti et al. | 435/240.23 |
| 5,686,289 A | 11/1997 | Humes et al. | 435/240.2 |
| 5,750,329 A | 5/1998 | Quinn et al. | 435/1.1 |
| 5,759,830 A | 6/1998 | Vacanti et al. | 435/180 |
| 5,770,193 A | 6/1998 | Vacanti et al. | 424/93.7 |
| 5,770,417 A | 6/1998 | Vacanti et al. | 435/180 |
| 5,800,537 A | * 9/1998 | Bell | 623/11 |
| 5,851,833 A | 12/1998 | Atala | 435/378 |
| 5,855,610 A | 1/1999 | Vacanti et al. | 623/11 |
| 5,858,721 A | 1/1999 | Naughton et al. | 435/69.1 |
| 5,863,531 A | 1/1999 | Naughton et al. | 424/93.7 |
| 5,916,265 A | 6/1999 | Hu | 623/11 |
| 5,962,325 A | 10/1999 | Naughton et al. | 435/395 |
| 6,018,024 A | * 1/2000 | Seubert et al. | 530/350 |

FOREIGN PATENT DOCUMENTS

| WO | 8803785 | 6/1988 |
|---|---|---|
| WO | 8901967 | 3/1989 |
| WO | WO 96/09372 | 3/1996 |
| WO | 9809582 | 3/1998 |
| WO | WO 98/46165 | 10/1998 |

OTHER PUBLICATIONS

Atala, A. et al., "Formation of Urothelial Structures in Vivo From Dissociated Cells Attached to Biodegradable Polymer Scaffolds in Vitro," *The Journal of Urology*, vol. 148, 658–62 (Aug. 1992).

Atala, A. et al., "Implantation in Vivo and Retrieval of Artificial Structures Consisting of Rabbit and Human Urothelium and Human Bladder Muscle," *The Journal of Urology*, vol. 150, 608–12 (Aug. 1993).

Atala, A. et al., "Injectable Alginate Seeded with Chondrocytes as a Potential Treatment for Vesicoureteral Reflux," *The Journal of Urology*, vol. 150, 745–7 (Aug. 1993).

Ben-Ze'ev, A. et al., "Cell–cell and Cell–matrix Interactions Differentially Regulate the Expression of Hepatic and Cytoskeletal Genes in Primary Cultures of Rat Hepatocytes," *PNAS*, vol. 85, 2161–5 (Apr. 1988).

Bissell, D. et al., "Interactions of Rat Hepatocytes with Type IV Collagen, Fibronectin and Laminin Matrices. Distinct Matrix–controlled Modes of Attachment and Spreading," *European Journal of Cell Biology*, vol. 40, 72–8 (1986).

Burke, J., "The Effects of the Configuration of an Artificial Extracellular Matrix on the Development of a Functional Dermis," *The Role of Extracellular Matrix in Development*, Alan R. Liss, Inc., eds. (NY), 351–55 (1984).

Cilento, B. et al., "Phenotypic and Cytogenetic Characterization of Human Bladder Urothelia Expanded in Vitro," *The Journal of Urology*, vol. 152, 665–70 (Aug. 1994).

Culliton, B., "Gore Tex Organoids and Genetic Drugs," *Science*, vol. 246, 747–9 (Nov., 10, 1989).

Davis, G. et al., "Human Amnion Membrane Serves as a Substratum for Growing Axons in Vitro and in Vivo," *Science*, vol. 236, 1106–9 (May 29, 1987).

Ebata, H. et al., "Liver Regeneration Utlilizing Hepatocytes Transplanted into the Rat Spleen," *Surg Forum*, vol. 29, 338–40 (1978).

Fontaine, M. et al., "Transplantation of Genetically Altered Hepatocytes Using Cell–Polymer Constructs," *Transplantation Proceedings*, vol. 25, No. 1, 1002–4 (Feb. 1993).

Gilbert, J. et al., "Cell Transplantation of Genetically Altered Cells on Biodegradable Polymer Scaffolds in Syngeneic Rats," *Transplantation*, vol. 56, No. 2, 423–7 (Aug. 1993).

Henry, E.W. et al., "Nerve Regeneration Through Biodegradable Polyester Tubes," *Experimental Neurology*, vol. 90, 652–76 (1985).

(List continued on next page.)

*Primary Examiner*—David M. Naff
(74) *Attorney, Agent, or Firm*—Thomas J. Engellenner; Jasbir Sagoo; Nutter, McClennen & Fish, LLP

(57) ABSTRACT artificial organs are reconstructed using a three-dimensional scaffold produced by decellularizing biostructures from a donor organ. The three-dimensional scaffold is perfused with isolated endothelial cells that develop to produce an endothelial tissue layer with a primitive vascular system that sustains the growth and development of a second cultured cell population. When grown in the three-dimensional scaffold containing the endothelial tissue layer, with the primitive vascular system, the cells of the second cell population proliferate, mature and differentiate into neomorphic organ structures that are analogous to their in vivo counterparts.

38 Claims, 7 Drawing Sheets

OTHER PUBLICATIONS

Humes, H.D. et al., "Replacement of Renal Function in Uremic Animals With a Tissue–Engineered Kidney," *Nature Biotechnology*, vol. 17, 451–5 (May 1999).

Ingber, D. et al., "Endothelial Growth Factors and Extracellular Matrix Regulate DNA Synthesis Through Modulation of Cell and Nuclear Expansion," *In Vitro Cellular & Developmental Biology*, vol. 23, No. 5, 387–94 (May 1987).

Jauregui, H.O. et al., "Attachment and Long Term Survival of Adult Rat Hepatocytes in Primary Monolayer Cultures: Comparison of Different Substrata and Tissue Culture Media Formulations," *In Vitro Cellular & Developmental Biology*, vol. 22, No. 1, 13–22 (Jan. 1986).

Langer, R. and Moses, M., "Biocompatible Controlled Release Polymers for Delivery of Polypeptides and Growth Factors," *Journal of Cellular Biochemistry*, vol. 45, 340–5 (1991).

Michalopoulos, G. and Pitot, H.C., "Primary Culture of Parenchymal Liver Cells on Collagen Membranes," *Experimental Cell Research*, vol. 94, 70–8 (1975).

Mooney, D. and Vacanti, J., "Tissue Engineering Using Cells and Synthetic Polymers," *Transplantation Reniews*, vol. 7, No. 3, 153–62 (Jul. 1993).

Naughton, B. et al., "Long–term Growth of Rat Bone Marrow Cells in a Three–dimensional Matrix," *The Anatomical Record*, vol. 218, 97A (1987).

Nikolovski, J. et al., "Design Engineering of a Bioartificial Renal Tubule Cell Therapy Device," *Cell Transplantation*, vol. 8, 351–64 (1999).

O'Connor, N. et al., "Grafting of Burns with Cultured Epithelium Prepared from Autologous Epidermal Cells," *The Lancet*, 75–8 (Jan. 10, 1981).

Puelacher, W.C. et al., "Tissue–engineered Growth of Cartilage: The Effect of Varying the Concentration of Chondrocytes Seeded Onto Synthetic Polymer Matrices," *Int. J. Oral Maxillofac. Surg.*, vol. 23, 49–53 (1994).

Reid, L. et al., "Long–term Cultures of Normal Rat Hepatocytes on Liver Biomatrix," *Annals New York Academy of Sciences*, 70–6 (1980).

Rhine, W. et al., "Polymers for Sustained Macromolecule Release: Procedures to Fabricate Reproducible Delivery Systems and Control Release Kinetics," *Journal of Pharmaceutical Sciences*, vol. 69, No. 3, 265–70 (Mar. 1980).

Rosen, H.B. et al., "Bioerodible Polyanhydrides for Controlled Drug Delivery," *Biomaterials*, vol. 4, 131–3 (Apr. 1983).

Sawada, N. et al., "Effects of Extracellular Matrix Components on the Growth and Differentiation of Cultured Rat Hepatocytes," *In Vitro Cellular & Developmental Biology*, vol. 23, No. 4, 267–73 (Apr. 1987).

Seckel, B.R. et al., "Nerve Regeneration Through Synthetic Biodegradable Nerve Guides: Regulation by the Target Organ," *Plastic and Reconstructive Surgery*, vol. 74, No. 2, 173–81 (Aug. 1984).

Shine, H.D. et al., "Cultured Peripheral Nervous System Cells Support Peripheral Nerve Regeneration Through Tubes in the Absence of Distal Nerve Stump," *Journal of Neuroscience Research*, vol. 14, 393–401 (1985).

da Silva, C. et al., "An In Vivo Model to Quantify Motor and Sensory Peripheral Nerve Regeneration Using Bioresorbable Nerve Guide Tubes," *Brain Research*, vol. 342, 307–15 (1985).

Tachibana, M. et al., "Ureteral Replacement Using Collagen Sponge Tube Grafts," The Journal of Urology, vol. 133, 866–9 (May 1985).

Takeda, T. et al., "Hepatocyte Transplantation in Biodegradable Polymer Scaffolds Using the Dalmation Dog Model of Hyperuricosuria," *Transplantation Proceedings*, vol. 27, No. 1, 635–6 (Feb. 1995).

Thompson, J. et al., "Heparin–binding Growth Factor 1 Induced the Formation of Organoid Neovascular Structures in vivo," *PNAS*, vol. 86, 7928–32 (Oct. 1989).

Thompson, J.A. et al., "Implantable Bioreactors: Modern Concepts of Gene Therapy," *Current Communications in Molecular Biology: Therapeutic Peptides and Proteins*, Cold Spring Harbor Laboratory, eds., 143–7 (1989).

Urry, D. and Pattanaik, A., "Elastic Protein–based Materials in Tissue Reconstruction," *Annals New York Academy of Sciences*, vol. 831,32–46 (Dec. 31, 1997).

Uyama, S. et al., "Delivery of Whole Liver–equivalent Hepatocyte Mass Using Polymer Devices and Hepatotrophic Stimulation," *Transplantation*, vol. 55, No. 4, 932–5 (Apr. 1993).

Walton, R. and Brown, R., "Tissue Engineering of Biomaterials for Composite Reconstruction: An Epidermental Model," *Annals of Plastic Surgery*, vol. 30, No. 2, 105–10 (Feb. 1993).

International Search Report, PCT/US00/33891, issued Mar. 26, 2001.

* cited by examiner

CULTURING DIFFERENT CELL POPULATIONS ON A DECELLULARIZED NATURAL BIOSTRUCTURE FOR ORGAN RECONSTRUCTION

BACKGROUND OF THE INVENTION

The technical field of this invention is reconstruction of artificial organs by perfusing cultured cell populations into decellularized scaffolds formed from harvested animal or cadaver organs. The invention is particularly useful in constructing artificial kidneys for implantation.

Acute renal failure refers to the disruption of normal kidney function. This clinical condition arises due to a variety of mechanisms including infections, circulatory failure (shock), vascular blockage, glomerulonephritis, and obstruction to urine flow. Acute renal failure frequently arises as a complication of abdominal or vascular surgery. Of particular clinical importance are cases of acute renal failure associated with trauma, sepsis, postoperative complications, or medication, particularly antibiotics.

Post-operative complications such as infections, are overcome by the use of complex drugs such as antibiotics. Unfortunately, these same drugs can be toxic to the kidneys, particularly in elderly persons. Due to the increasing age of the hospital population and advances in complicated medical and surgical techniques, cases of acute renal failure are expected to increase in number and significance unless advances in treatment are made.

Treatment of acute renal failure typically involves dialysis, which removes the waste products and chemicals from the blood system. Despite some advances, the mortality rate associated with kidney disease still has not changed in many years. While dialysis provides a way to filter waste products and chemicals, the typical treatment regime poses a significant inconvenience to most patients. Usually treatment regimes involve lengthy time periods during which the patient is attached to the dialysis unit. The dialysis procedure is also repeated multiple times during a week. In many cases, the patient experiences side effects, such as muscle cramps and hypotension associated with the rapid change in the patient's body fluid.

Kidney transplantation provides an alternative to dialysis. This involves replacing the patient's kidney with a healthy kidney from a donor, if one becomes available. The implanted kidney then functions as the patient's own kidney to filter blood and produce urine. Unfortunately, kidney rejection is a significant risk associated with transplantation, even with a good histocompatibility match. Immunosuppressive drugs such as cyclosporin and FK506 are usually given to the patient to prevent rejection. However, these immunosuppressive drugs have a narrow therapeutic window between adequate immunosuppression and toxicity. Prolonged immunosuppression can weaken immune systems, which can lead to a threat of infections developing. In some instances, even immunosuppression is not enough to prevent kidney rejection.

In an attempt to avoid the problems associated with dialysis and kidney transplantations, various methods have been reported in which the patients own kidney cells have been cultured in vitro. For example, U.S. Pat. No. 5,429,938 issued to Humes describes a method of reconstructing renal tubules using cultured kidney cells. The reconstructed renal tubules can be implanted into the patient.

Naughton et al. disclosed a three-dimensional tissue culture system in which stromal cells are laid over a polymer support system (see U.S. Pat. No. 5,863,531).

Vacanti et al. have disclosed methods for culturing cells in a three-dimensional matrix made of a biodegradable polymer. Organ cells are first cultured within the matrix and then implanted into the patient.

The above methods rely on shaping the support structure into the desired configuration of the organ. The correct three-dimensional configuration is essential for the reconstructed organ to function properly in vivo. Not only is the shape required to fit into the body cavity, but the shape also creates the necessary microenvironment for the cultured cells to grow and proliferate.

Therefore, a need exists for reconstructing artificial organs with the same three-dimensional infra-structure as the native organ. There is also a need to reconstruct an artificial organ for use as a permanent replacement of an organ.

SUMMARY OF THE INVENTION

The present invention provides compositions and methods for reconstructing artificial organs using a three-dimensional scaffold generated by decellularizing a natural biostructure. The three-dimensional scaffold is perfused with a population of cultured endothelial cells which attach to the three-dimensional scaffold and develop into an endothelial tissue layer. Continued growth and differentiation of the endothelial cells on the three-dimensional scaffold results in the formation of a primitive vascular system in the endothelial tissue layer. The primitive vascular system can then develop into a mature vascular system, and can also support the growth and development of additional cultured cell populations. The three-dimensional scaffold and the endothelial tissue layer with the primitive vascular system can be used to culture a variety of different cells and tissues in vitro and in vivo.

Accordingly, in one aspect, the invention features a method of reconstructing an artificial organ construct comprising:

perfusing a population of cultured endothelial cells into a three-dimensional scaffold formed by decellularizing a natural biostructure, such that endothelial cells attach to the three-dimensional scaffold;

culturing the endothelial cells in the three-dimensional scaffold until the endothelial cells produce an endothelial tissue layer comprising a primitive vascular system;

seeding at least one further second population of cultured cells into the three-dimensional scaffold such that the second cell population attaches to the endothelial tissue layer comprising the primitive vascular system and differentiates into a neomorphic organ structure.

During in vitro growth, the endothelial cells develop and produce an endothelial tissue layer comprising a primitive vascular system which envelopes the three-dimensional scaffold. The three-dimensional scaffold is composed of a biocompatible, non-degradable material. The endothelial tissue layer also provides a primitive vascular system that is capable of developing into a mature vascular system supports the growth and development of additional cultured cell populations. When grown in this three-dimensional scaffold, the proliferating cells mature and segregate properly to form tissues analogous to counterparts found in vivo.

The invention is based, in part, on the discovery that growth of endothelial cells in decellularized three-dimensional scaffolds will sustain active proliferation of additional cell populations. This may be due, in part, to the increased surface area of the natural biostructure-derived scaffold which permits in a prolonged period of active proliferation of endothelial cells. The prolonged proliferation enables the endothelial cells to develop to provide a primitive vascular system. The primitive vascular system subsequently provides support for the growth and development of additional cultured cell populations. In addition, the three-dimensionality of the decellularized biostructure allows for a spatial distribution which is the same as conditions in vivo, thus allowing for the formation of a microenvironment that is conducive for cellular maturation and migration. Optimal cell growth and development arises when the infrastructure of the microenvironment resembles the infra-structure of a natural organ. This provides the correct spacial distances that enable cell-cell interaction to occur. The growth of cells in the presence of this scaffold may be further enhanced by adding proteins, glycoproteins, glycosaminoglycans and a cellular matrix.

In one embodiment, the natural biostructure is an organ selected from the group consisting of heart, kidney, liver, pancreas, spleen, bladder, ureter and urethra. In another embodiment, the natural biostructure is a part of an organ selected from the group consisting of heart, kidney, liver, pancreas, spleen, bladder, ureter and urethra. In a preferred embodiment, the artificial organ construct is an artificial kidney construct. In another preferred embodiment, the three-dimensional scaffold is derived from a decellularized mammalian kidney. In another preferred embodiment, the endothelial cells are human endothelial cells. In another preferred embodiment, the second population comprises human kidney cells.

In another aspect, the invention features a method of treating a subject with an organ disorder comprising:
 implanting a three-dimensional scaffold formed by decellularizing a natural biostructure perfused with a population of cultured endothelial cells, such that the endothelial cells attach to the three-dimensional scaffold to produce an endothelial tissue layer comprising a primitive vascular system, and at least one further second. population of cultured cells, such that the second cell population attaches to an endothelial tissue layer comprising a primitive vascular system and differentiates into a neomorphic organ structure; and
 monitoring the subject for a modulation in the organ disorder.

In another aspect, the invention features an artificial organ construct comprising: a three-dimensional scaffold formed by decellularizing a natural biostructure, perfused with a population of cultured endothelial cells, such that the endothelial cells attach to the three-dimensional scaffold to produce an endothelial tissue layer comprising a primitive vascular system, and at least one further second population of cultured cells, such that the second cell population attaches to the an endothelial tissue layer comprising a primitive vascular system and differentiates into a neomorphic organ structure.

In another aspect, the invention features a method for reconstructing an artificial kidney construct comprising:
 perfusing a population of cultured endothelial cells into a three-dimensional scaffold formed by decellularizing a mammalian kidney, such that endothelial cells attach to the three-dimensional scaffold;
 culturing the endothelial cells in the three-dimensional scaffold until the endothelial cells produce an endothelial tissue layer comprising a primitive vascular system;
 seeding a population of cultured kidney cells into the three-dimensional scaffold such that the kidney cell population attaches to the endothelial tissue layer comprising the primitive vascular system and differentiates into nephron structures.

In another aspect, the invention features a method of treating a subject with a kidney disorder comprising:
 implanting a three-dimensional scaffold formed by decellularizing a mammalian kidney perfused with a population of cultured endothelial cells, such that the endothelial cells attach to the three-dimensional scaffold to produce an endothelial tissue layer comprising a primitive vascular system, and a population of cultured kidney cells, such that the kidney cell population attaches to the endothelial tissue layer comprising the primitive vascular system and differentiates into nephron structures; and monitoring the subject for a modulation in the kidney disorder.

In another aspect, the invention features an artificial kidney construct comprising:
 a three-dimensional scaffold formed by decellularizing a mammalian kidney perfused with a population of cultured endothelial cells, such that the endothelial cells attach to the three-dimensional scaffold to produce an endothelial tissue layer comprising a primitive vascular system, and a population of cultured kidney cells, such that the kidney cell population attaches endothelial tissue layer comprising the primitive vascular system and differentiates into nephron structures.

In another aspect, the invention features a method for screening a compound that modulates kidney cells comprising:
 providing an artificial kidney construct with a three-dimensional scaffold formed by decellularizing a mammalian kidney, perfused with a population of cultured endothelial cells, such that the endothelial cells attach to the three-dimensional scaffold to produce an endothelial tissue layer comprising primitive vascular system, and a population of cultured kidney cells, such that the kidney cell population attaches to the endothelial tissue layer comprising the primitive vascular system and differentiates into nephron structures;
 contacting the artificial kidney construct with a library of test compounds;
 selecting from the library of test compounds a compound of interest that modulates kidney cells.

In one embodiment, the modulator is cytotoxic to the kidney cells. In another embodiment, the modulator is therapeutic to the kidney cells. In one embodiment, the compound is a chemical agent, or a pharmaceutical agent.

In another aspect, the invention features a method for processing an aqueous solution comprising:
 providing an artificial kidney construct having a three-dimensional scaffold formed by decellularizing a mammalian kidney perfused with a population of cultured endothelial cells, such that the endothelial cells attach to the three-dimensional kidney scaffold to produce an endothelial tissue layer comprising a primitive vascular system, and a population of cultured kidney cells, such that the kidney cell population attaches to endothelial tissue layer comprising the primitive vascular system and differentiates into nephron structures;
 delivering the aqueous solution to the luminal side of the artificial kidney construct;
 collecting a processed aqueous solution from the abluminal side of the artificial kidney construct.

In one embodiment, the aqueous solution is unfiltered blood and the processed aqueous solution is filtered blood.

DESCRIPTION OF THE DRAWINGS

The invention will be more fully understood from the following detailed description taken in conjunction with the accompanying drawings, in which.

DETAILED DESCRIPTION

Figure 1:
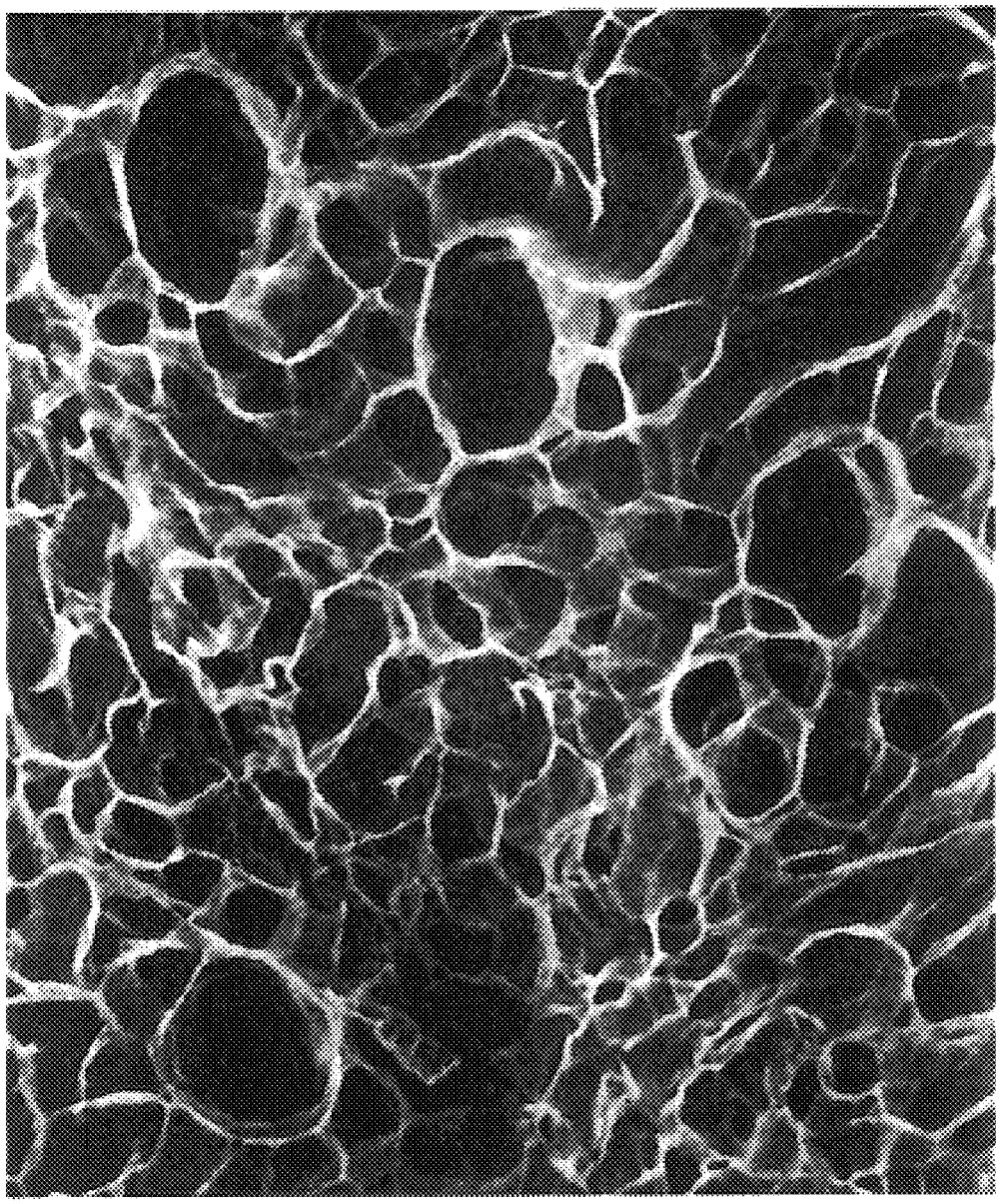
FIG. 1 is an electron micrograph depicting a decellularized kidney matrix.

So that the invention may more readily be understood, certain terms are first defined:

The term "attach" or "attaches" as used herein refers to cells adhered directly to the three-dimensional scaffold or to cells that are themselves attached to other cells.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infrastructure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra.

The phrase "three-dimensional scaffold" as used herein refers to the residual infrastructure formed when a natural biostructure, e.g. an organ, is decellularized. This complex, three-dimensional, scaffold provides the supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ. This three-dimensional scaffold is perfused with a population of cultured endothelial cells which grow and develop to provide an endothelial tissue layer comprising a primitive vascular system that is capable of developing into a mature vascular system. The endothelial tissue layer and the primitive vascular system is also capable of supporting growth and development of at least one additional cultured cell population.

The term "primitive vascular system" as used herein refers to the early stages of development of a vascular system comprising blood vessels that supply blood to the tissue structures.

The term "natural biostructure" as used herein refers to a biological arrangement found within a subject, for example, organs, that include but are not limited, heart, kidney, liver, pancreas, spleen, bladder, ureter and urethra. The term "natural biostructure" is also intended to include parts of biostructures, for example parts of organs, for example, the renal artery of a kidney.

The term "neomorphic organ structure" as used herein refers to a component of parenchymous tissue. The neomorphic organ structure is created when cells that make up the parenchyma tissue differentiate into various compounds. For example, a natural kidney has the medulla and cortical regions, which are produced when kidney cells differentiate to produce nephron structures. The nephron structure has the Bowman's capsule, distal convulated tubule, loop of Henlè, proximal convulated tubule and collecting ducts.

The term "subject" as used herein is intended to include living organisms in which an immune response is elicited. Preferred subjects are mammals. Examples of subjects include but are not limited to, humans, monkeys, dogs, cats, mice, rates, cows, horses, pigs, goats and sheep.

The present invention provides compositions and methods for reconstructing artificial organs. Reconstruction of artificial organs comprises perfusing a population of cultured endothelial cells into the scaffold formed by decellularizing a natural biostructure, such that endothelial cells attach to the three-dimensional scaffold;

culturing the endothelial cells in the three-dimensional scaffold until the endothelial cells produce an endothelial tissue layer comprising a primitive vascular system;

seeding at least one further second population of cultured cells into the three-dimensional scaffold such that the second cell population attaches to the endothelial tissue layer comprising the primitive vascular system and differentiates into a neomorphic organ structure.

The artificial organ is reconstructed by using a decellularized natural biostructure as the three-dimensional scaffold onto which a cultured endothelial cell population are perfused. The natural biostructure can be any biological arrangement found within a subject, for example an organ, e.g.,heart, kidney, liver, pancreas, spleen, bladder, ureter and urethra., or a part of the organ.

I Natural Biostructures

The natural biostructure, e.g. an organ, can be obtained from a donor of the same species as the subject, for example, a human cadaver kidney for a human kidney recipient. The natural biostructure can also be obtained from a different species which includes, but is not limited to, monkeys, dogs, cats, mice, rats, cows, horses, pigs, goats and sheep. The natural biostructure can also be obtained from the subject requiring a reconstructed organ, for example, a subject with one dysfunctional kidney and one functional kidney, can have the dysfunctional kidney removed and decellularized using the process described below. The decellularized kidney of the subject can be used as the three-dimensional scaffold to reconstruct an artificial kidney using cultured endothelial cells and kidney cells isolated from the subject. The artificial reconstructed kidney can be implanted back into the subject for further development.

II Decellularization of Biostructures

Biostructures, e.g., whole organs, or parts of organs can be decellularized by removing the entire cellular and tissue content from the organ as described in Example 1. The decellularization process comprises a series of sequential extractions. One key feature of this extraction process is that harsh extraction that may disturb or destroy the complex infrastructure of the biostructure, be avoided. The first step involves removal of cellular debris and solubilization of the cell membrane. This is followed by solubilization of the nuclear cytoplasmic components an the nuclear components.

Preferably, the biostructure, e.g., an organ, is decellularized by removing the cell membrane and cellular debris surrounding the organ using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the organ, agitating the organ, or stirring the organ in a suitable volume of fluid, e.g., distilled water. In one preferred embodiment, the gentle mechanical disruption method includes magnetically stirring (e.g., using a magnetic stir bar and a magnetic plate) the organ in a suitable volume of distilled water until the cell membrane is disrupted and the cellular debris has been removed from the organ.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of nonionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl β-D-glucopuranoside, n-heptyl β-D glucopyranoside, n-Octylα-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem, Hoechst Celanese Corp., 1987. In one preferred embodiment, the non-ionic surfactant is the Triton series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentrations ranges non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, comprising consisting of the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

III Culturing Cells

The reconstructed artificial organ can be an allogenic, where the cell populations are derived from the subject's own tissue. For example, endothelial cells can be derived from the subject's skin, liver, pancreas, arteries, veins, umbilical cord, or placental tissues. Kidney cells can also be derived from the subject's dysfunctional kidney and cultured in vitro.

The reconstructed artificial organ can also be xenogenic, where cell populations are derived from a mammalian species that are different from the subject. For example the different cells can be derived from organs of mammals such as monkeys, dogs, cats, mice, rats, cows, horses, pigs, goats and sheep.

Such organs can be obtained by appropriate biopsy or upon autopsy. Cadaver organs may be used to provide a supply of endothelial cells and elements. The isolated cells are preferably autologous cells, obtained by biopsy from the subject. For example, a biopsy of skeletal muscle from the arm, forearm, or lower extremities, or smooth muscle from the area treated with local anaesthetic with a small amount of lidocaine injected subcutaneously, and expanded in culture. The biopsy can be obtained using a biopsy needle, a rapid action needle which makes the procedure quick and simple. The small biopsy core of either skeletal or smooth muscle can then be expanded and cultured. Cells from relatives or other donors of the same species can also be used with appropriate immunosuppression.

Methods for the isolation and culture of cells are discussed by Freshney, Culture of Animal Cells. A Manual of Basic Technique, 2d Ed., A. R. Liss, Inc., New York, 1987, Ch. 9, pp. 107–126. Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the organ, the use of grinders, blenders, sieves, homogenizers, pressure cells, or insonators to name but a few.

Preferred cell types include, but are not limited to, kidney cells, urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepatocytes, Islet cells, cells present in the intestine, and other parenchymous cells, nerve cells, osteoblasts and other cells forming bone or cartilage. In a preferred embodiment human endothelial cells are isolated. In another preferred embodiment human kidney cells are isolated. Kidney cells from all developmental stages, such as, fetal, neonatal, juvenile to adult may be used.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting (see e.g. Freshney, (1987) Culture of Animal Cells. A Manual of Basic Techniques, 2d Ed., A. R. Liss, Inc., New York, Ch. 11 and 12, pp. 137–168). For example, endothelial cells may be enriched by fluorescence-activated cell sorting. Similarly, kidney cells may also be enriched.

Cell fractionation may also be desirable, for example, when the donor has diseases such as kidney cancer or metastasis of other tumors to the kidney. A kidney cell population may be sorted to separate malignant kidney cells or other tumor cells from normal noncancerous kidney cells. The normal noncancerous kidney cells, isolated from one or more sorting techniques, may then be used for kidney reconstruction.

Isolated cells can be cultured in vitro to increase the number of cells available for infusion into the three-dimensional scaffold. The use of allogenic cells, and more preferably autologous cells, is preferred to prevent tissue rejection. However, if an immunological response does occur in the subject after implantation of the reconstructed artificial organ, the subject may be treated with immunosuppressive agents such as, cyclosporin or FK506, to reduce the likelihood of rejection. In certain embodiments, chimeric cells, or cells from a transgenic animal, can be perfused onto the three-dimensional scaffold.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery. Endothelial and/or kidney cells could be transfected with specific genes prior to infusion into the three-dimensional scaffold. The artificial reconstructed organ could carry genetic information required for the long term survival of the host or the reconstructed artificial organ.

The endothelial cells grown on the scaffold may be genetically engineered to produce gene products beneficial to transplantation, e.g., anti-inflammatory factors, e.g., anti-GM-CSF, anti-TNF, anti-IL-1, and anti-IL-2. Alternatively, the endothelial cells may be genetically engineered to "knock out" expression of native gene products that promote inflammation, e.g., GM-CSF, TNF, IL-1, IL-2, or "knock out" expression of MHC in order to lower the risk of rejection. In addition, the endothelial cells may be genetically engineered for use in gene therapy to adjust the level of gene activity in a patient to assist or improve the results of tissue transplantation.

Methods for genetically engineering cells with retroviral vectors, polyethylene glycol, or other methods known to those skilled in the art can be used. These include using expression vectors which transport and express nucleic acid molecules in the cells. (See Geoddel; *Gene Expression Technology: Methods in Enzymology* 185, Academic Press, San Diego, Calif. (1990).

Vector DNA is introduced into prokaryotic or eukaryotic cells via conventional transformation or transfection techniques. Suitable methods for transforming or transfecting host cells can be found in Sambrook et al. *Molecular Cloning: A Laboratory Manual*, 2nd Edition, Cold Spring Harbor Laboratory press (1989), and other laboratory textbooks.

Cells grown on the three-dimensional scaffold and endothelial tissue layer comprising a primitive vascular system, in accordance with the present invention, grow in multiple layers, forming a cellular matrix that resembles physiologic conditions found in vivo. The three-dimensional scaffold and endothelial tissue layer comprising the primitive vascular system, can support the proliferation of different types of cells and the formation of a number of different tissues. Examples include, but are not limited to, bone marrow, skin, liver, pancreas, kidney, adrenal and neurological tissue, as well as tissues of the gastrointestinal and genitourinary tracts, and the circulatory system.

When the artificial reconstructed organ is to be used for transplantation or implantation in vivo, it may be preferable to obtain the endothelial cells or parenchymous cells from the individual who is to receive the transplant or implant. This approach might be especially advantageous where immunological rejection of the transplant and/or graft versus host disease is likely.

Once perfused onto the three-dimensional scaffold, the endothelial cells will proliferate and develop on the scaffold to form an endothelial tissue layer. During in vitro culturing, the endothelial cells develop and differentiate to produce a primitive vascular system which is capable of developing into a mature vascular system, and is also capable of supporting the growth of parenchyma cells perfused into the three-dimensional scaffold. Importantly, because the three-dimensional scaffold has an infrastructure that permits culture medium to reach the endothelial tissue layer and the parenchyma cells, the different cell populations continue to grow, divide, and remain functionally active. The parenchyma cells proliferate, and differentiate into neomorphic organ structures that have a morphology which resembles the analogous structure in vivo.

It is important to recreate, in culture, the cellular microenvironment found in vivo for the particular organ being reconstructed. The invention provides a method in which a decellularized organ is used to reconstruct an artificial organ.

Using a decellularized organ retains the complex infrastructure that enables perfused cultured cell populations to attach to the three-dimensional scaffold. Retaining an infrastructure that is similar or the same as an in vivo organ creates the optimum environment for cell-cell interactions, development and differentiation of cell populations. The extent to which the endothelial cells and parenchyma cells are grown prior to use in vivo may vary depending on the type of organ being reconstructed.

The invention provides a method of reconstructing an artificial organ using a three-dimensional scaffold with an endothelial tissue layer comprising a primitive vascular system. This scaffold supports the maturation, development and differentiation, of additional cultured cells in vitro to form components of adult tissues analogous to their in vivo counterparts. The three-dimensional scaffold allows optimum cell-cell interactions, thereby allowing a more natural formation of cellular phenotypes and a tissue microenvironment. The three-dimensional scaffold also allows endothelial cells to continue to grow actively, proliferate and differentiate to produce a primitive vascular system. This primitive vascular system is capable of further development and is also capable of supporting the growth, proliferation and differentiation of additional cultured cells populations, for example, cultured parenchyma tissue cell populations, thereby establishing a localized microenvironment that is more conducive to an in vivo tissue.

IV. Establishment of the Three-Dimensional Endothelial Tissue

The three-dimensional scaffold is produced by the process of decellularization, as described in Section II. The decellularized three-dimensional scaffold retains the shape of the decellularized biostructure and allows cultured cells to attach to it and grow on, or in it. The decellularized three-dimensional scaffold can be pre-treated with, for example, collagen, prior to perfusion of cultured endothelial cells in order to enhance the attachment of endothelial cells to the three-dimensional scaffold.

Endothelial cells are perfused into the scaffold using needles placed in localized positions in the three-dimensional scaffold. These endothelial cells may be derived from organs, such as, skin, liver, and pancreas, which can be obtained by biopsy (where appropriate) or upon autopsy. Endothelial cells can also be obtained from any appropriate cadaver organ. The endothelial cells can be expanded by culturing them in vitro to the desired cell density prior to infusion into the three-dimensional scaffold.

Endothelial cells may be readily isolated by disaggregating an appropriate organ or tissue which is to serve as the source of the cells. This may be accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include, but are not limited to, trypsin, chymotrypsin, collagenase, elastase, and/or hyaluronidase, DNase, pronase, and dispase. Mechanical disruption can also be accomplished by a number of methods including, but not limited to, the use of grinders, blenders, sieves, homogenizers, pressure cells, or insonators to name but a few. (See e.g. Freshney, (1987) Culture of Animal Cells. A Manual of Basic Technique, 2d Ed., A. R. Liss, Inc., New York, Ch. 9, pp. 107–126.)

After reducing the tissue to a suspension of individual cells, the suspension can be fractionated into subpopulations from which the endothelial cells can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. (See e.g. Freshney, (1987) Culture of Animal Cells. A Manual of Basic Techniques, 2d Ed., A. R. Liss, Inc., New York, Ch. 11 and 12, pp. 137–168.)

The growth of cells in the three-dimensional scaffold may be enhanced by adding, or coating the three-dimensional scaffold with proteins (e.g., collagens, elastic fibers, reticular fibers) glycoproteins, glycosaminoglycans (e.g., heparan sulfate, chondroitin-4-sulfate, chondroitin-6-sulfate, dermatan sulfate, keratin sulfate, etc.), a cellular matrix, and/or other materials.

After perfusion of the endothelial cells, the three-dimensional scaffold should be incubated in an appropriate nutrient medium. Many commercially available media such as RPMI 1640, Fisher's, Iscove's, McCoy's, Dulbecco's medium, and the like, may be suitable for use. The culture medium should also be changed periodically to remove the used media, depopulate released cells, and add fresh media. It is important to grow the endothelial cells to a stage where an endothelial tissue layer comprising a primitive vascular system has developed prior to perfusion of the endothelial tissue layer with the parenchyma cells.

V. Perfusion of Parenchyma Cells onto Three-Dimensional Endothelial Scaffold

Once the three-dimensional endothelial tissue layer has reached the appropriate degree of growth and developed to produce a primitive vascular system, additional populations of cultured cells such as parenchymal cells can be perfused onto the endothelial tissue layer. Parenchyma cells perfused onto the endothelial tissue can be incubated to allow the cells to adhere to the endothelial tissue layer. The parenchyma cells can be cultured in vitro in culture medium to allow the cells to grow and develop until the cells resemble a morphology and structure similar to the that of the native tissue. Growth of parenchyma cells on the endothelial tissue layer results in the differentiation of parenchyma cells into the appropriate neomorphic organ structures.

Alternatively, after perfusing the three-dimensional parenchyma cells, the scaffold can be implanted in vivo without prior in vitro culturing of the parenchyma cells. The parenchyma cells chosen for perfusion will depend upon the organ being reconstructed. For example, reconstruction of a kidney will involve infusing cultured endothelial cells into a decellularized kidney three-dimensional scaffold, which is cultured until they develop into endothelial tissue layer comprising a primitive vascular system. The endothelial tissue can then be perfused with cultured kidney cells and cultured in vitro until the kidney cells begin to differentiate to form nephron structures.

The parenchyma cells may be obtained from cell suspensions prepared by disaggregating the desired tissue using standard techniques as described above. The cells may then be cultured in vitro to a desired density. After attaining the desired density, the cultured cells can be used to perfuse the three-dimensional scaffold with the endothelial tissue layer.

The cells will proliferate, mature, and differentiate on the endothelial tissue layer. The choice of parenchyma cells will depend on the organ being reconstructed for example, when reconstructing an artificial kidney, the three-dimensional kidney scaffold and endothelial tissue layer is perfused with cultured kidney cells. When reconstructing an artificial liver, the three-dimensional liver scaffold and endothelial tissue layer is perfused cultured hepatocytes. When reconstructing an artificial pancreas, the three-dimensional pancreatic scaffold and endothelial tissue layer is perfused with cultured pancreatic endocrine cells. For a review of methods which may be utilized to obtain parenchymal cells from various tissues, see, Freshney, (1987) Culture of Animal Cells. A Manual of Basic Technique, 2d Ed., A. R. Liss, Inc., New York, Ch. 20, pp. 257–288. Cells are cultured until they differentiate to produce neomorphic organ structures that resemble the morphology of the native in vivo tissue Growth factors and regulatory factors can be added to the media to enhance, alter or modulate proliferation and cell maturation and differentiation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

VI. Uses of the Reconstructed Artificial Organs

The reconstructed artificial organs of the invention can be used in a variety of applications. For example, The reconstructed artificial organs can be implanted into a subject. Implants, according to the invention, can be used to replace or augment existing tissue. For example, to treat a subject with a kidney disorder by replacing the dysfunctional kidney of the subject with an artificial reconstructed kidney. The subject can be monitored after implantation of the artificial kidney, for amelioration of the kidney disorder.

The reconstructed artificial organs can be used in vitro to screen a wide variety of compounds, for effectiveness and cytotoxicity of pharmaceutical agents, chemical agents, growth/regulatory factors. The cultures can be maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the reconstructed artificial organs may be assessed.

The reconstructed artificial organs may be used in vitro to filter aqueous solutions, for example, a reconstructed artificial kidney may be used to filter blood. Using the reconstructed kidney provides a system with morphological features that resemble the in vivo kidney products. This system may be suitable for hemodialysis. and may be more effective in removing blood solutes of intermediate molecular weight which ordinary hemodialysis systems are incapable of removing. The system may also be useful for hemofilteration to remove water and low molecular weight solutes from blood. The artificial kidney may be maintained in vitro and exposed to blood which may be infused into the luminal side of the artificial kidney. The processed aqueous solution may be collected from the abluminal side of the artificial kidney. The efficiency of filtration may be assessed by measuring the ion, or metabolic waste content of the filtered and unfiltered blood.

The reconstructed artificial organs of the invention may be used as a vehicle for introducing genes and gene products in vivo to assist or improve the results of the transplantation and/or for use in gene therapies. For example, the cultured endothelial cells can be engineered to express gene products. The cells can be engineered to express gene products transiently and/or under inducible control or as a chimeric fusion protein anchored to the endothelial cells, for example, a chimeric molecule composed of an intracellular and/or transmembrane domain of a receptor or receptor-like molecule, fused to the gene product as the extracellular domain. In another embodiment, the endothelial cells can be genetically engineered to express a gene for which a patient is deficient, or which would exert a therapeutic effect. The genes of interest engineered into the endothelial cells or parenchyma cells need to be related to the disease being treated. For example, for a kidney disorder, the endothelial, or cultured kidney cells can be engineered to express gene products that would ameliorate the kidney disorder.

The endothelial or parenchyma cells can be engineered using a recombinant DNA construct containing the gene of interest which is used to transform or transfect endothelial or parenchymas cells. The three-dimensional scaffold and endothelial tissue layer comprising a primitive vascular system which expresses the active gene product, could be implanted into an individual who is deficient for that product. For example, genes that prevent or ameliorate symptoms of various types of vascular, genitourinary tract, hernia, gastrointestinal diseases, or kidney diseases may be under-expressed or down regulated under disease conditions. The level of gene activity may be increased by either increasing the level of gene product present or by increasing the level of the active gene product which is present in the three-dimensional scaffold and endothelial tissue. The three-dimensional culture which expresses the active target gene product can then be implanted into the patient who is deficient for that product.

The three-dimensional cultures containing such genetically engineered endothelial or parenchyma cells are then implanted into the subject to allow for the amelioration of the symptoms of the disease. The gene expression may be under the control of a non-inducible (i.e., constitutive) or inducible promoter. The level of gene expression and the type of gene regulated can be controlled depending upon the treatment modality being followed for an individual patient.

Also within the scope of the invention are compositions and methods of reconstructing artificial organs comprising one population of cultured cells. Alternatively the reconstructed artificial constructs comprise multiple layers of cultured cell populations. Organs that can be reconstructed include, but are not limited to, heart, kidney, liver, pancreas, spleen, bladder, ureter and urethra.

By including and sustaining the parenchyma tissues in three-dimensional scaffold and endothelial tissue layer comprising the primitive vascular system, the parenchyma tissues can differentiate into neomorphic organ structures that have special structural and functional properties required for proper physiological functioning in vivo. The reconstructed artificial organs simulate the corresponding in vivo biological structure and can serve as a replacement for the damaged or diseased in vivo organ.

Other embodiments and used of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

EXAMPLES

Example 1

Preparation of a Decellularized Kidney

The following method describes a process for removing the entire cellular content of an organ or tissue without destroying the complex three-dimensional infrastructure of the organ or tissue. A kidney, was surgically removed from a C7 black mouse using standard techniques for tissue removal. The kidney was placed in a flask containing a suitable volume of distilled water to cover the isolated kidney. A magnetic stir plate and magnetic stirrer were used to rotate the isolated kidney in the distilled water at a suitable speed for 24–48 hours at 4° C. This process removes the cellular debris and cell membrane surrounding the isolated kidney.

After this first removal step, the distilled water was replaced with a 0.05% ammonium hydroxide solution containing 0.5% Triton X-100. The kidney was rotated in this solution for 72 hours at 4° C. using a magnetic stir plate and magnetic stirrer. This alkaline solution solubilized the nuclear and cytoplasmic components of the isolated kidney. The detergent Triton X-100, was used to remove the nuclear components of the kidney, while the ammonium hydroxide solution was used to lyse the cell membrane and cytoplasmic proteins of the isolated kidney.

The isolated kidney was then washed with distilled water for 24–48 hours at 4° C. using a magnetic stir plate and magnetic stirrer. After this washing step, removal of cellular components from the isolated was confirmed by histological analysis of a small piece of the kidney. If necessary, the isolated kidney was again treated with the ammonium hydroxide solution containing Triton X-100 until the entire cellular content of the isolated kidney was removed. After removal of the solubilized components, a collagenous three-dimensional framework in the shape of the isolated kidney was produced.

This decellularized kidney was equilibrated with 1× phosphate buffer solution (PBS) by rotating the decellularized kidney overnight at 4° C. using a magnetic stir plate and magnetic stirrer. After equilibration, the decellularized kidney was lyophilized overnight under vacuum. The lyophilized kidney was sterilized for 72 hours using ethylene oxide gas. After sterilization, the decellularized kidney was either used immediately, or stored at 4° C. or at room temperature until required. Stored organs were equilibrated in the tissue culture medium overnight at 4° C. prior to seeding with cultured cells.

Example 2

Isolation of Kidney Cells

Small kidneys, for example, from one week old C7 black mice, were decapsulated, dissected, minced and suspended in Dulbecco's Modified Eagles's Medium (DMEM; Sigma, St. Louis, Mo.) containing 15 mM Hepes, pH 7.4 and 0.5 $\mu$g/ml insulin, 1.0 mg/ml collagenase and 0.5 mg/ml dispase, a neutral protease from *Bacillus polymyxal* (Boehringer Mannheim, Indianapolis, Ind.).

Large kidneys, for example, swine kidneys, were arterially perfused at 37° C. for 10 minutes with calcium free Eagles minimum essential medium within three hours of extraction. The kidneys were then perfused with 0.5 mg/ml collagenase (Type IV, Sigma, St. Louis, Mo.) in the same buffer supplemented with 1.5 mM $MgCl_2$ and 1.5 mM $CaCl_2$. The kidneys were then decapsulated, dissected, minced and suspended in Dulbecco's Modified Eagles's Medium (DMEM; Sigma, St. Louis, Mo.) containing 15 mM Hepes, pH 7.4 and 0.5 $\mu$/ml insulin, 1.0 mg/ml collagenase and 0.5 mg/ml dispase, a neutral protease from *Bacillus polymyxal* (Boehringer Mannheim, Indianapolis, Ind.).

The kidney cell suspension, from either large or small kidneys, was gently agitated in a water bath for 30 minutes at 37° C. The cells and fragments were recovered by centrifugation at 50 g for five minutes. The pellets were resuspended in DMEM containing 10% fetal bovine serum (Biowhittaker, Walkersville, Md.) to stop proteolysis, and the turbid solution was passed through sterile 80 mesh nylon screens to eliminate large fragments. The cells were recovered by centrifugation and washed twice with calcium free Dulbecco's Modified Eagles's Medium.

Example 3

In vitro Culturing of Kidney Cells.
(i) Isolation of Rat Tail Collagen

Tendon was stripped from rat tails and stored in 0.12 M acetic acid in deionized water in 50 ml tubes. After 16 hours at 4° C. overnight.

Dialysis bags were pretreated to ensure a uniform pore size and removal of heavy metals. Briefly, the dialysis bag is submerged in a solution of 2% sodium bicarbonate and 0.05% EDTA and boiled for ten minutes. Multiple rinses of distilled water was used to remove the sodium bicarbonate and 0.05% EDTA.

The 0.12 M acetic acid solution comprising rat tendons was placed in treated dialysis bags and dialyzed for two or three days to remove acetic acid. The dialysis solution was changed every 3 to 4 hours.
(ii) Coating Tissue Culture Plates The culture flasks, 75 $cm^2$, were coated with a solution containing about 30 $\mu$g/ml collagen (Vitrogen or rat tail collagen), about 10 $\mu$g/ml human fibronectin (Sigma, St. Louis, Mo.) and about 10 $\mu$g/ml bovine serum albumin (Sigma, St. Louis, Mo.) in a total volume of about 2 ml of supplemented medium by incubation at 37° C. for 3 hours.
(iii) Cell Culture Digested single suspended renal cells were plated on, a modified collagen matrix at a concentration of about $1 \times 10^6$ cells/ml and grown in DMEM supplemented with about 10% fetal bovine serum, about 5 $\mu$g/ml bovine insulin, about 10 $\mu$g/ml transferrin, about 10 $\mu$g/ml sodium selenite, about 0.5 $\mu$M hydrocortisone, about 10 ng/ml prostaglandin $E_2$, about 100 units/ml penicillin G, about 100 $\mu$g/ml streptomycin (Sigma, St. Louis, Mo.) in a 5% $CO_2$ incubator at about 37° C.

Confluent monolayers, were subcultured by treatment with about 0.05% trypsin, about 0.53 mM EDTA (Gibco BRL, Grand Island, N.Y.) in calcium ion free phosphate buffer saline (PBS) (about 1.51 mM $KH_2PO_4$, about 155.17 mM NaCl, about 2.8 mM $Na_2HPO.7H_2O$). Cells may be cultured any time from the first passage by suspension in about 10% DMSO in culture medium for freezing and storage in liquid medium.
(iv) Treatment of a Decellularized Kidney with Collagen The decellularized kidney structure was perfused with a solution containing about 30 $\mu$g/ml collagen (Vitrogen or rat tail collagen), about 10 μg/ml human fibronectin (Sigma, St. Louis, Mo.) and about 10 μg/ml bovine serum albumin (Sigma, St. Louis, Mo.) in supplemented medium. The collagen perfused decellularized kidney structure was placed into an incubator with 1 ml concentrated ammonium hydroxide (about 28% to about 30% $NH_4OH$, Sigma, St. Louis, Mo.) for 30 minutes to raise the pH and to promote the gelling of the collagen. After ammonium hydroxide treatment, the decellularized kidney structure was washed extensively with isotonic medium to neutralize the pH of the decellularized kidney structure before use.

Example 4

In vitro Culturing of Endothelial Cells

Endothelial cells, were isolated form a dissected vein. Perivenous heparin/papaverine solution (3 mg papaverine HCl diluted in 25 ml Hanks balanced salt solution (HBSS) containing 100 units of heparin (final conc. 4u/ml)), was used to improve endothelial cell preservation. A proximal silk loop was placed around the vein and secured with a tie. A small venotomy was made proximal to the tie and the tip of vein cannula was inserted and secured in place with a second tie. A second small venotomy was made beyond the proximal tie and the vein was gently flushed with Medium 199/heparin solution Medium 199 (M-199) supplemented with 20% fetal bovine serum, ECGF (100 μg/ml), L-glutamine, heparin (Sigma, 17.5 u/ml) and antibiotic-antimycotic), to remove blood and blood clots. Approximately 1 ml of a collagenase solution (0.2% Worthington type I collagenase dissolved in 98 ml of M-199, 1 ml of FBS, 1 ml of PSF, at 37° C. for 15–30 min, and filter sterilized), was used to flush through the dissected vein. The collagenase solution was also used to gently distend the vein and the distended vein was placed into 50 ml tube containing Hank's Balanced Salt Solution (HBSS). The tube containing the collagenase distended vein was incubated for 12 minutes at 37° C. to digest the inner lining of the vein. After digestion, the contents of the vein, which contain the endothelial cells, were removed into a sterile 15 ml tube. The endothelial cell suspension was centrifuged at 125× g for 10 minutes. Endothelial cells were resuspended in 2 ml of Dulbec Co.'s Modified Eagle Media with 10% FBS and penicillin/streptomycin (DMEM/10%FBS) and plated into a 24 well plate coated with 1% difcogelatin. The endothelial cells were incubated overnight at 37° C.

After overnight incubation, the cells were rinsed with HBSS and placed in 1 ml of fresh DMEM/10%FBS. The media was changed 3 times a week. When cultures reached confluence (after 3–7 days), the confluent monolayers were subcultured by treatment with 0.05% trypsin, 0.53 mM EDTA, for 3–5 min until the cells dispersed. The dispersed cells were plated onto culture dishes coated with 0.1% difcogelatin at a 1:4–1:6 split ratio. The endothelial cells were expanded until sufficient cell quantities were achieved. Cells were trypsinized, collected, washed and counted for seeding.

Example 5

Reconstruction of an Artificial Kidney

A kidney was surgically removed and decellularized as described in Example 1. The decellularized kidney structure, as shown in FIG. 1, was used as a scaffold for reconstructing an artificial kidney. Endothelial cells were cultured and expanded in vitro as described in Example 4. The endothelial cell suspension was gently perfused using needles placed into the decellularized kidney structure. The decellularized kidney structure was perfused with approximately $10\times10^6$ cells per $cm^3$ and was incubated at 37° C. under 5% $CO_2$ until the cells attached and grew on the matrix. The structure was incubated at 37° C. under 5% $CO_2$ for about 3 days until a layer of endothelial cells with a primitive vascular system was established. Media was changed at frequent intervals, for example, about every day, about every two days or about every three days.

Figure 2:
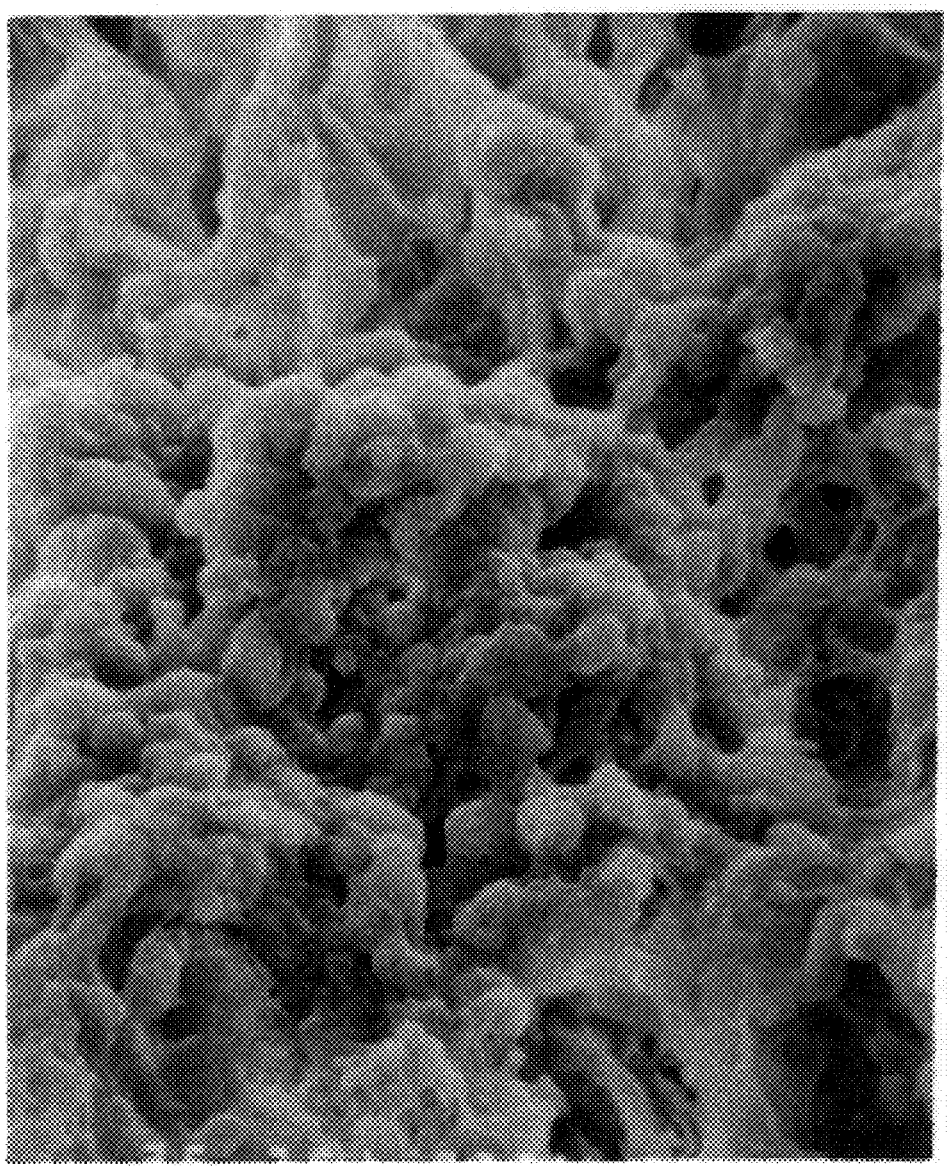
FIG. 2 is an election micrograph depicting in vitro growth of renal cells seeded on a decellularized kidney matrix.

Kidney cells were cultured and expanded in vitro for 10 days as described in Example 3. The cells were harvested by trypsin digestion using 0.05% trypsin, about 0.53 mM EDTA (Gibco BRL, Grand Island, N.Y.) in calcium ion free phosphate buffer saline (PBS) (about 1.51 mM $KH_2PO_4$, about 155.17mM NaCl, about 2.8 mM $Na2HPO.7H_2O$). After digestion for 10 minutes at 37° C. the cells were resuspended in DMEM media at approximately $5\times10^6$ cells/ml. The kidney cell suspension was then gently perfused over the endothelial layer using needles placed into the decellularized structure. The decellularized kidney structure, perfused with approximately cells $10\times10^6$ cells $cm^3$ and were incubated at 37° C. under 5% $CO_2$ until the cells attached and grew (see, FIG. 2). The structure was incubated at 37° C. under 5% $CO_2$ for about 3 days to about 10 days, until the kidney cells begin to differentiate into kidney tubule cells.

An artificial kidney can also be reconstructed using a bioreactor system. Single suspended renal cells were seeded on a decellularized kidney matrix. The cells were allowed to attach onto the matrix wall for 2 hours at 37° C. After incubation was completed, medium was slowly added to the flask to cover the entire matrix, taking care not to disturb the cells within the matrix. The medium was changed daily, or more frequently depending on the level of lactic acid. On day 4 after initial seeding, the cell-matrix system was engaged in a circulating bioreactor system. The infusion tubing was connected to the main renal artery and the returning tubing was connected to the main renal vein. Additional single renal cells were seeded through the main renal arterial matrix. After the infusion of the additional cells, the bioreactor was discontinued for 2 hours to allow the cells to attach to the matrix. Infusion of medium was initiated with a low infusion rate to avoid cell disruption. The cells were allowed to firmly adhere to the matrix for 3 or 4 days.

After the renal cells have been seeded into the decellularized kidney, smooth muscle cells were seeded. The external main renal artery and vein were seeded directly on the surface of the vessels. Internal vascular structures were seeded through the main renal artery using infusion techniques known to the skilled artisan. After infusion of the smooth muscle cells, the circulation through the bioreactor was interrupted for 2 hours to allow the smooth muscle cells to adhere. After 2 hours, medium was slowly infused through the circulating bioreactor system at a low rate to prevent agitation of the attached smooth muscle cells. The smooth muscle cells took at least 2 days to organize on the vascular matrix.

After the smooth muscle are organized, vascular endothelial cells were seeded on the luminal surface of blood vessels through the main renal artery. The circulation in the bioreactor was interrupted for 2 hours to allow the cells to settle and adhere to the vascular luminal wall. The culture medium was then infused through the circulating bioreactor system at a low rate to avoid agitating the cells. The cells took at least 2 days to organize on the vascular matrix.

Urothelium and smooth muscle cells, composing the collecting system, were seeded using a retrograde seeding technique. Single suspended urothelial cells were seeded through the ureter and smooth muscle cells were seeded from the serosa side. Medium was changed regularly during the culturing process and should cover the entire cell-matrix. The artificial kidney construct is ready for implantation when the infused medium stops leaking through the bioreactor.

Example 6

Implantation of the Reconstructed Kidney into a Recipient

Figure 3:
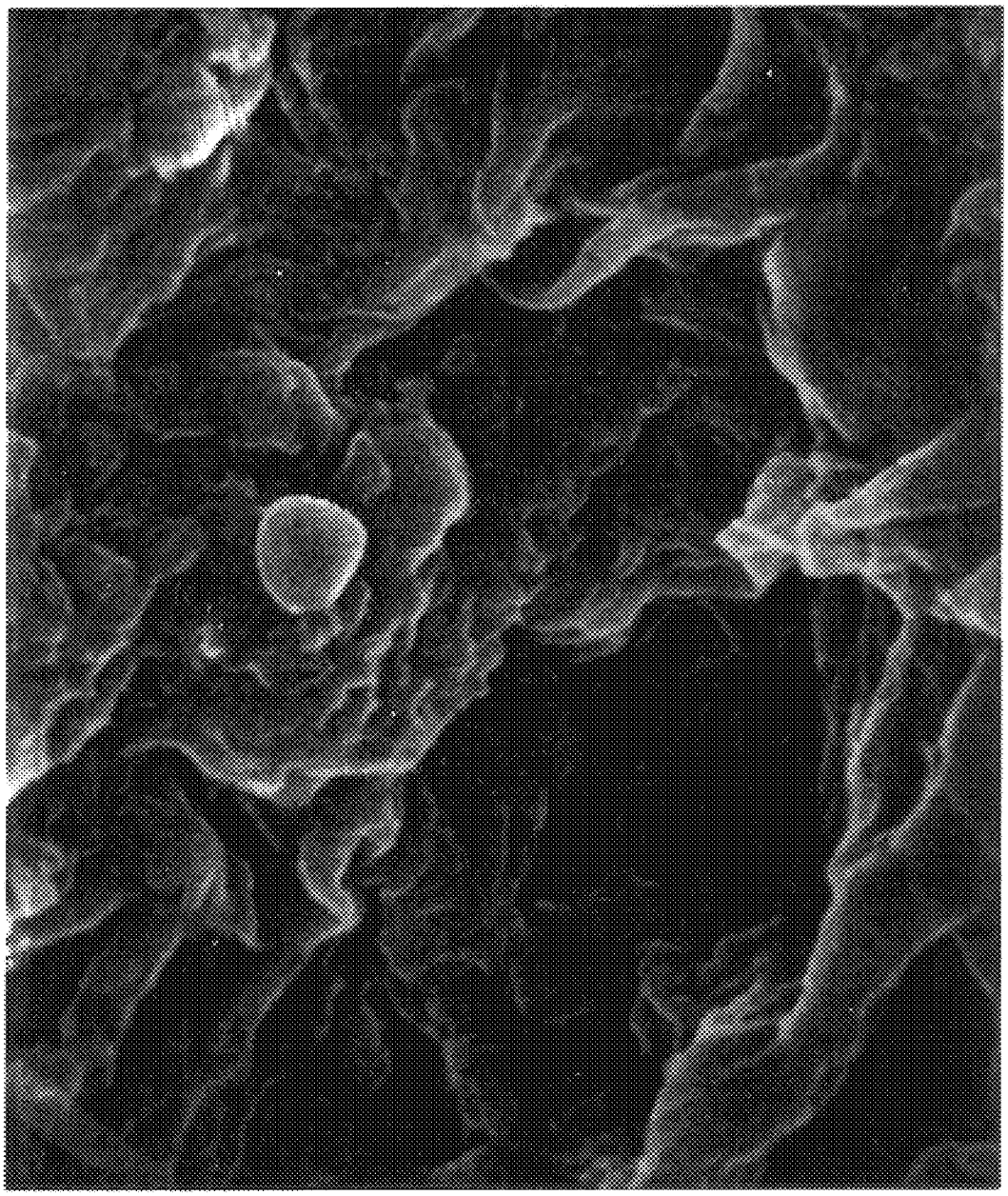
FIG. 3 is an electron micrograph depicting in vivo growth of renal cells seeded on a decellularized kidney matrix.

The reconstructed kidney comprising a primitive vascular system and kidney cells differentiated into kidney tubule cells was implanted into an athymic mouse. Athymic mice may be purchased from commercially from suppliers such as Jackson Laboratories of Bar Harbor, Me. Animals were monitored for the in vivo function of the reconstructed kidney, by observing urine output. The reconstructed kidney demonstrated the continued growth and proliferation of renal cells after in vivo implantation (see, FIG. 3) Animals were sacrificed at about two, about four, and about eight weeks post-implantation and the reconstructed kidney was retrieved and analyzed.

Retrieved specimens were examined grossly and histologically with hematoxylin and eosin. Immunohistochemical stains for osteopontin, fibronectin and alkaline phosphatase were performed to determine the cell types and their architecture in vivo. Human fibronectin monoclonal antibody (Sigma, St. Louis, Mo.) was used against fibronectin matrix. Rhodamine-conjugated goat anti-mouse (Boehringer Mannheim, Indianapolis, Ind.) was used as a secondary antibody. Immunocytochemical staining for osteopontin was performed with a polyclonal antibody. Antibodies were produced in New Zealand white rabbits using standard procedures (Harlow and Lane, Antibodies a laboratory manual, 1988, Cold Spring Harbor Press, Cold Spring Harbor) and used at a 1:5000 dilution ratio. Goat anti-rabbit antibody conjugated with FITC (Boehringer Mannheim, Indianapolis, Ind.) was used as a secondary antibody. Immunohistochemical stain for alkaline phosphatase using nitroblue tetrazolium and 5-Bromo-4-choloro-3-indolyl phosphate (Sigma, St. Louis, Mo.) was performed. Filtrate collected from the prosthetic kidney was straw yellow in color. Analysis of the filtrate for uric acid level was performed using a uric acid detection kit (Sigma Diagnostics, St. Louis, Mo.).

Figure 4:
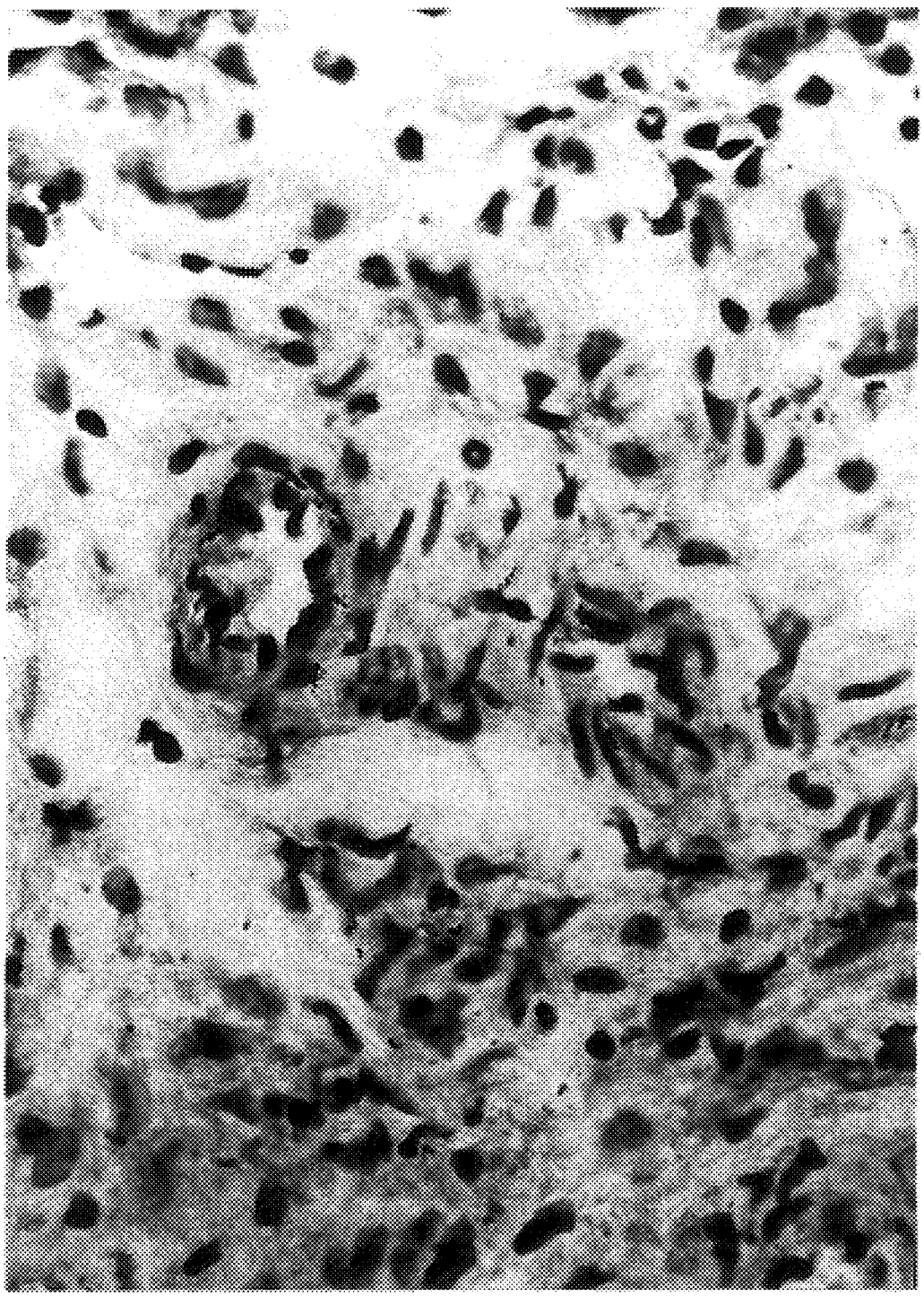
FIG. 4 is a photograph demonstrating the formation of tubular structures by cells seeded within a decellularized kidney matrix.
Figure 5:
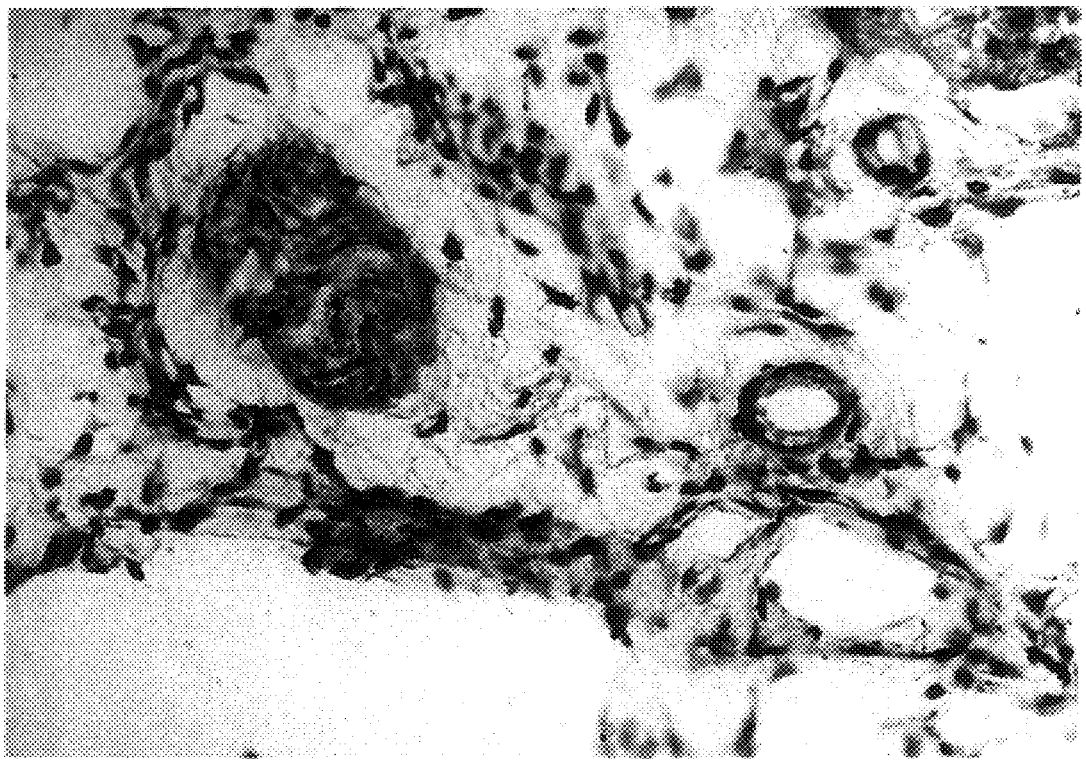
FIG. 5 is a photograph demonstrating the formation of glomerulus and tubular structures by renal cells seeded within a decellularized kidney matrix.
Figure 6:
FIG. 6 is a photograph demonstrating the morphology of in vivo cells lining the vessel wall of the decellularized kidney matrix.
Figure 7:
FIG. 7 is a photograph demonstrating the viability of cells from a reconstructed kidney, implanted in vivo that bound to fluorescent binder, DIL.

The fluid in the reconstructed kidney was collected. Histological examination of the implanted reconstructed kidney revealed extensive vascularization, formation of glomeruli and highly organized tubule-like structures (see, FIGS. 4 and 5) with a morphology analogous of an native kidney (see, FIG. 6). The renal cells in the reconstructed kidney remained viable post-implantation, determined by their ability to bind the fluorescent marker, DIL. (see, FIG. 7). Immunocytochemical staining with anti-osteopontin antibody which is secreted primarily by proximal and distal tubule cells stained the tubular sections positively. Immunohistochemical staining for alkaline phosphatase stained proximal tubule like structures positively. The yellow fluid collected from the newly formed renal unit contained 66 mg/dl uric acid, as compared to 2 mg/dl in plasma, suggesting that these tubules are capable of unidirectional secretion and concentration of uric acid.

What is claimed is:

1. An artificial organ construct comprising:
   a three-dimensional scaffold of connective tissue formed by decellularizing a natural biostructure to remove cellular content, which has been perfused with a first population of isolated and cultured endothelial cells, such that the endothelial cells attach to the three-dimensional scaffold to produce an endothelial tissue layer comprising a vascular system, and at least one second population of cultured cells that is different from the population of cultured endothelial cells, such that the second cell population attaches to the endothelial tissue layer comprising a vascular system and differentiates into a neomorphic organ structure.

2. The artificial organ of claim 1, wherein the natural biostructure is an organ selected from the group consisting of heart, kidney, liver, pancreas, spleen, bladder, ureter and urethra.

3. The artificial organ of claim 1, wherein the natural biostructure is a part of an organ selected from the group consisting of heart, kidney, liver, pancreas, spleen, bladder, ureter and urethra.

4. The artificial organ of claim 1, wherein the artificial organ construct is an artificial kidney construct.

5. The artificial organ of claim 1, wherein the scaffold is derived from a decellularized mammalian kidney.

6. The artificial organ construct of claim 1, wherein the endothelial cells are human endothelial cells.

7. The artificial organ construct of claim 1, wherein the second cell population comprises human kidney cells.

8. An artificial kidney construct comprising:
   a three-dimensional scaffold of connective tissue formed by decellularizing a mammalian kidney to remove cellular content, which has been perfused with a population of isolated and cultured endothelial cells, such that the endothelial cells attach to the three-dimensional scaffold to produce an endothelial tissue layer comprising a vascular system, and a population of cultured kidney cells, such that the kidney cell population attaches to the endothelial tissue layer comprising the vascular system and differentiates into nephron structures.

9. The artificial kidney of claim 8, wherein the endothelial cells are human endothelial cells.

10. The artificial kidney of claim 8, wherein the kidney cells are human kidney cells.

11. A method of treating a subject with an organ disorder comprising:
    implanting a three-dimensional scaffold of connective tissue formed by decellularizing a natural biostructure to remove cellular content, which has been perfused with a first population of isolated and cultured endothelial cells, such that the endothelial cells attach to the three-dimensional scaffold to produce an endothelial tissue layer comprising a vascular system, and at least one second population of cultured cells that is different from the population of cultured endothelial cells, such that the second cell population attaches to an endothelial tissue layer comprising a vascular system and differentiates into a neomorphic organ structure; and
    monitoring the subject for a modulation in the organ disorder.

12. The method of claim 11, wherein the natural biostructure is an organ selected from the group consisting of heart, kidney, liver, pancreas, spleen, bladder, ureter and urethra.

13. The method of claim 11, wherein the natural biostructure is a part of an organ selected from the group consisting of heart kidney, liver, pancreas, spleen, bladder, ureter and urethra.

14. The method of claim 11, wherein the artificial organ construct is an artificial kidney construct.

15. The method of claim 11, wherein the scaffold is derived from a decellularized mammalian kidney.

16. The method of claim 11, wherein the endothelial cells are human endothelial cells.

17. The method of claim 11, wherein the second cell population comprises human kidney cells.

18. A method of treating a subject with a kidney disorder comprising;
implanting a three-dimensional scaffold of connective tissue formed by decellularizing a mammalian kidney to remove cellular content, which has been perfused with a population of isolated and cultured endothelial cells, such that the endothelial cells attach to the three-dimensional scaffold to produce an endothelial tissue layer comprising a vascular system, and a population of cultured kidney cells, such that the kidney cell population attaches to the endothelial tissue layer comprising the vascular system and differentiates into nephron structures; and monitoring the subject for a modulation in the kidney disorder.

19. The method of claim 18, wherein the endothelial cells are human endothelial cells.

20. The method of claim 18, wherein the kidney cells are human kidney cells.

21. A method for screening a compound that modulates kidney cells comprising:
providing an artificial kidney construct with a three-dimensional scaffold of connective tissue formed by decellularizing a mammalian kidney to remove cellular content, which has been perfused with a population of isolated and cultured endothelial cells, such that the endothelial cells attach to the three-dimensional scaffold to produce an endothelial tissue layer comprising vascular system, and a population of cultured kidney cells, such that the kidney cell population attaches to the endothelial tissue layer comprising the vascular system and differentiates into nephron structures;
contacting the artificial kidney construct with a library of test compounds;
selecting from the library of test compounds a compound of interest that modulates kidney cells.

22. The method of claim 21, wherein the modulator is cytotoxic to the kidney cells.

23. The method of claim 21, wherein the modulator is therapeutic to the kidney cells.

24. The method of claim 21, wherein the compound is a chemical agent.

25. The method of claim 21, wherein the compound is a pharmaceutical agent.

26. A method for processing an aqueous solution comprising:
providing an artificial kidney construct having a three-dimensional scaffold of connective tissue formed by decellularizing a mammalian kidney to remove cellular content, which has been perfused with a population of isolated and cultured endothelial cells, such that the endothelial cells attach to the three-dimensional kidney scaffold to produce an endothelial tissue layer comprising a vascular system, and a population of cultured kidney cells, such that the kidney cell population attaches to the endothelial tissue layer comprising the vascular system and differentiates into nephron structures;
delivering the aqueous solution to a luminal side of the artificial kidney construct;
collecting a processed aqueous solution from an abluminal side of the artificial kidney construct.

27. The method of claim 26, wherein the aqueous solution is unfiltered blood.

28. The method of claim 26, wherein the processed aqueous solution is filtered blood.

29. A method of reconstructing an artificial organ construct comprising:
decellularizing a natural biostructure by removing cellular content to produce a three-dimensional scaffold of connective tissue:
perfusing a first population of isolated and cultured endothelial cells into the three-dimensional scaffold formed by decellularizing a natural biostructure, such that endothelial cells attach to the three dimensional scaffold;
culturing the endothelial cells in the scaffold until the endothelial cells produce an endothelial tissue layer comprising a vascular system;
seeding at least one second population of cultured cells that is different from the population of cultured endothelial cells into the three-dimensional scaffold such that the second cell population attaches to the endothelial tissue layer comprising the vascular system and differentiates into a neomorphic organ structure.

30. The method of claim 29, wherein the natural biostructure is an organ selected from the group consisting of heart, kidney, liver, pancreas, spleen, bladder, ureter and urethra.

31. The method of claim 29, wherein the natural biostructure is a part of an organ selected from the group consisting of heart, kidney, liver, pancreas, spleen, bladder, ureter and urethra.

32. The method of claim 29, wherein the artificial organ construct is an artificial kidney construct.

33. The method of claim 29, wherein the scaffold is derived from a decellularized mammalian kidney.

34. The method of claim 29, wherein the endothelial cells are human endothelial cells.

35. The method of claim 29, wherein the second cell population comprises human kidney cells.

36. A method of reconstructing an artificial kidney construct comprising:
decellularizing a mammalian kidney by removing cellular content to produce a three-dimensional scaffold of connective tissue;
perfusing a population of isolated and cultured endothelial cells into the three-dimensional scaffold formed by decellularizing a mammalian kidney, such that endothelial cells attach to the three-dimensional scaffold;
culturing the endothelial cells in the three-dimensional scaffold until the endothelial cells produce an endothelial tissue layer comprising a vascular system;
seeding a population of cultured kidney cells into the three-dimensional scaffold such that the kidney cell population attaches to the endothelial tissue layer comprising the vascular system and differentiates into nephron structures.

37. The method of claim 36, wherein the endothelial cells are human endothelial cells.

38. The method of claim 36, wherein the kidney cells are human kidney cells.

* * * * *